United States Patent [19]

Ostergard

[11] 4,168,698

[45] Sep. 25, 1979

[54] ENDOCERVICAL STRIP BIOPSY INSTRUMENT

[75] Inventor: Donald R. Ostergard, Rolling Hills Estates, Calif.

[73] Assignee: Professional Staff Association of the Los Angeles County Harbor General Hospital, Torrance, Calif.

[21] Appl. No.: 807,245

[22] Filed: Jun. 16, 1977

[51] Int. Cl.² ............................................. A61B 10/00
[52] U.S. Cl. ............................... 128/751; 128/305; 30/136; 30/279 R; 30/287; 30/353
[58] Field of Search ................. 128/2 B, 305, 305.1, 128/305.5, 307, 309–310, 315; 30/41, 41.6, 27, 136, 136.5, 279 R, 287, 353

[56] References Cited

U.S. PATENT DOCUMENTS

| 1,513,648 | 10/1924 | Sprigg | 30/41 |
|---|---|---|---|
| 2,275,022 | 3/1942 | Thomas | 30/41.6 |
| 2,293,171 | 8/1942 | Reardon | 128/309 |
| 2,715,899 | 8/1955 | MacLean | 128/2 B |
| 3,407,815 | 10/1968 | Abelson | 128/309 |
| 3,412,732 | 11/1968 | Simon | 128/305.5 |
| 3,415,251 | 12/1968 | Knapp et al. | 128/305.5 |
| 3,583,403 | 6/1971 | Pohl et al. | 128/305.5 |
| 3,683,892 | 8/1972 | Harris | 128/305 X |
| 3,797,505 | 3/1974 | Gilhaus et al. | 128/304 X |
| 4,043,322 | 8/1977 | Robinson | 128/2 B |

FOREIGN PATENT DOCUMENTS 1231083  5/1971  United Kingdom ..................... 128/305

Primary Examiner—Robert W. Michell
Assistant Examiner—Francis J. Jaworski
Attorney, Agent, or Firm—I. Morley Drucker

[57] ABSTRACT

The endocervical instrument of this invention comprises, generally, a handle and an elongated basket-like member removably mounted onto the handle. The basket-like member is elongated and generally of rectangular-shape as viewed in plan. The basket member has a wall surface defining an elongated cavity therewithin and an entrance into the cavity from one side of the basket member. One end of the basket member carries a blade means which preferably projects laterally with respect to the entrance to the elongated cavity of the basket member. The blade member projects laterally from the sidewalls defining the entrance to the cavity a sufficient distance to enable an endocervical tissue strip of approximately 1.5–2 mm., in depth, to be obtained as the blade member is drawn distally towards the external os of the endocervical canal. The floor of the basket member is preferably pivotally mounted to the basket member end portions or sidewalls, and each strip of endocervical tissue may be readily removed from the floor of the basket member—after the floor thereof is pivotally disengaged from its normally closed position.

5 Claims, 6 Drawing Figures

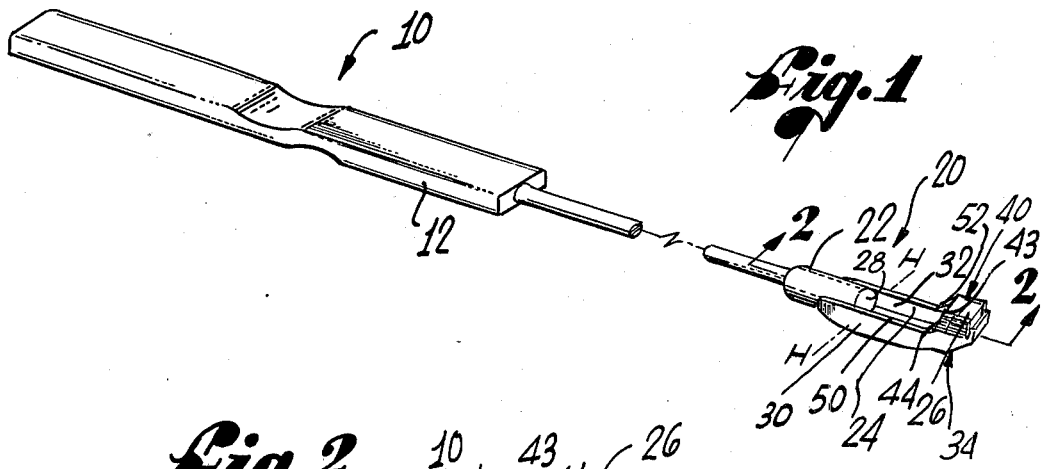
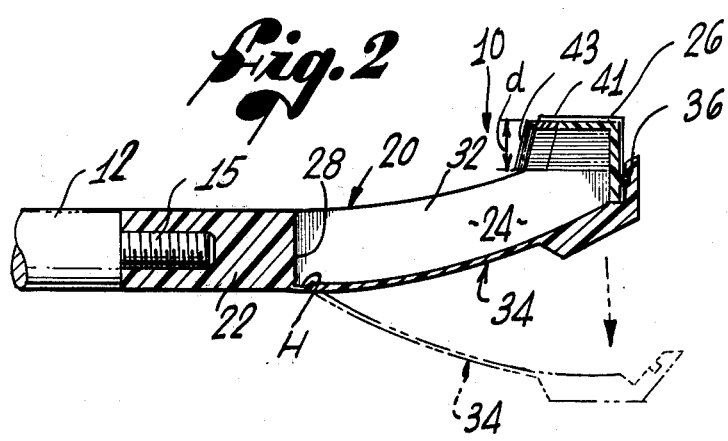
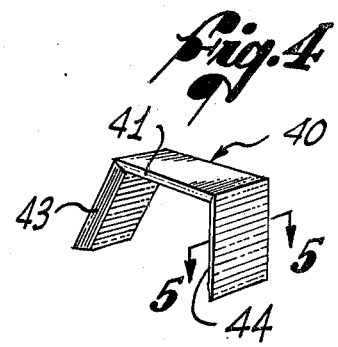
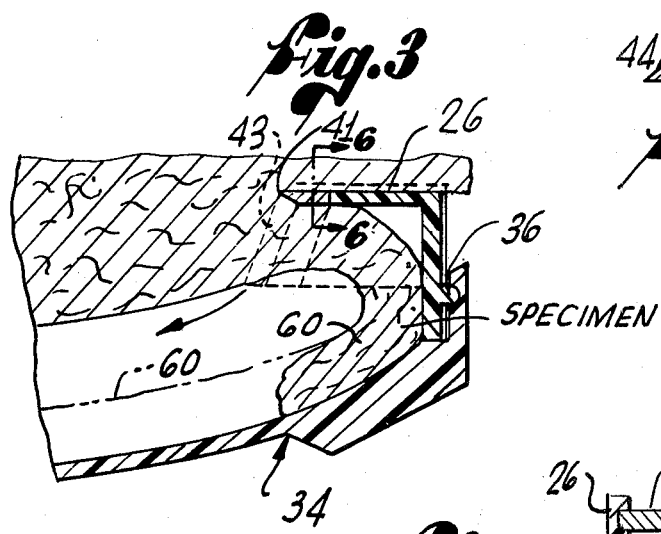
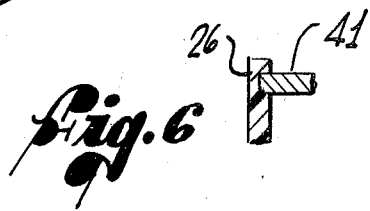

ENDOCERVICAL STRIP BIOPSY INSTRUMENT

BACKGROUND OF THE INVENTION

This invention relates to a device, or instrument, for obtaining a strip biopsy from the endocervical canal of the human uterine cervix.

Accurate endocervical histology is essential in the management of patients with abnormal Papanicolaou (Pap) smears to determine whether or not the endocervical canal is involved by the disease process. At the present time, upon evidence of an abnormal Pap smear, the patient is subjected to a surgical operative procedure in the hospital, under anesthesia, in which cone-shaped portions of tissue are taken from the endocervical canal for biopsy purposes. The instrument normally employed is a conventional scalpel. The routine procedure may cause extensive blood loss, is traumatic, time-consuming and expensive. The long term effects may also possibly give rise to possible infertility and/or cervical incompetence or stenosis during pregnancy due to the amount of tissue taken in such a biopsy procedure and the resulting scar tissue formation.

It has also been proposed, in order to avoid the hospitalization procedure above noted, to utilize an endocervical curette, normally used in a dilatement and curettage procedure, for the purpose of obtaining tissue material for a biopsy. The endocervical tissue scrapings normally obtained with such curettes are fragmented, non-coherent tissue, and do not include stroma (that tissue under the epithelial lining of the cervix uteri). Furthermore, the present endocervical curette designs do not enable a pathologist to receive a tissue specimen free of excessive blood or other contaminating debris. Fragmented, non-coherent, contaminated tissue is difficult to interpret histopathologically. Additionally, specimens of stroma tissue are needed for diagnosis of invasive cancer cells.

In addition to the above-described drawbacks of the present endocervical curettes, it is very difficult to maintain a very high degree of sharpness on their cutting edges under frequent use conditions.

The major objects of the present invention are to obviate the above-described drawbacks of the present curette design, so that relatively noncontaminated, coherent, elongated strips of relatively thick endocervical tissue (including stroma tissue) may be obtained for biopsy. These and other objects will become apparent from the following description of the invention.

BRIEF DESCRIPTION OF THE DRAWINGS

FIG. 1 is a fragmentary perspective view of the endocervical strip biopsy instrument of my invention;

FIG. 2 is a longitudinal cross-section thereof, taken along the line 2—2, the phantom line showing a second position of the instrument;

FIG. 3 is an enlarged view of a portion of FIG. 2 showing, schematically, the instrument in actual use;

FIG. 4 is a perspective view of the blade means prior to its embedment in the instrument proper;

FIG. 5 is a cross-sectional view of the blade means, taken along the line 5—5 of FIG. 4; and FIG. 6 is a transverse cross-sectional view taken along the line 6—6 of FIG. 3.

SUMMARY OF THE INVENTION

The endocervical instrument of this invention comprises, generally, a handle and an elongated basket-like member threadably mounted onto the handle. The basket-like member is elongated and generally of rectangular shape as viewed in plan. The basket member has a wall surface defining an elongated cavity therewithin and an entrance into the cavity from one side of the basket member. The proximal end of the basket member carries a blade means which preferably projects laterally with respect to the entrance to the elongated cavity of the basket member.

In use, the patient is first locally anesthetized, as by a paracervical block. The instrument of this invention is then inserted within the endocervical canal with the laterally projecting blade means extending just beyond the proximal tip of the canal and the edges of the sidewalls defining the entrance to the cavity pressed against the lining of the endocervical canal. The blade means is then moved distally along the endocervical lining towards the external os of the uterus with the edges of the sidewall acting as guide members. The distal movement of the blade means along the endocervical lining cuts a strip of endocervical tissue (of sufficient depth to include stroma) which strip will fall, through the entrance, into the cavity in a coherent relatively clean mass. Four endocervical biopsy strips are preferably obtained in successive cuts following the above surgical procedure.

The floor of the basket member is preferably pivotally mounted to the basket member end portions or sidewalls, and each strip of endocervical tissue may be readily removed from the basket member after the floor thereof is pivotally disengaged from its normally closed position. The blade member projects laterally from the sidewalls defining the entrance to the cavity, a sufficient distance to enable an endocervical tissue strips of a depth of approximately 1.5–2 mm. to be obtained as the blade member is drawn distally towards the external os of the endocervical canal.

After the above-surgical procedure, the tissue of the endocervical canal is either chemically or electrocauterized in a conventional manner to prevent bleeding.

The instrument of this invention may be re-used, after sterilization, if desired. No hospitalization, or relatively extensive surgical procedure would be required.

The blade member may assume various shapes, e.g., arcuate or inverted U-shape. If U-shaped, the angle measured between the sides of the blade member and the bridging portion thereof is approximately 90°–125°.

DETAILED DESCRIPTION OF THE INVENTION

The endocervical strip biopsy instrument of this invention is designated generally by the numeral 10. The instrument 10 has a handle 12 and a basket-like member 20 removably affixed to the handle 12 by means of screw 15 threaded onto the distal end portion 22 of basket member 20.

The basket member 20 is preferably made of a strong, rigid, moldable, plastic, such as a polypropylene and is formed with a plurality of wall surfaces defining an elongated cavity 24, the surfaces defining the elongated cavity 24 comprising a laterally projecting proximal end portion 26, the distal end portion 22 including a back-wall 28, sidewalls 30, 32 extending between the end portion 22, 26 and a floor member 34 extending between the end portions 22, 26. As can be seen in the drawings, sidewalls 30 and 32 define a side entrance into cavity 24, the entrance being generally coextensive with the cavity 24, as shown in FIG. 2. The floor member 34 is preferably, pivotally or hingedly mounted, about transverse axis H, the floor being removably affixed to proximal end portion 26 by means of a tongue and groove snap-fastener 36, or other suitable fastening device. The pivotal mounting, about transverse axis H is accomplished by thinning the plastic along the axis H, as shown, although it will be understood that other forms of pivotal mounting of the floor member 34 may be employed.

As shown in the drawings, the blade means 40 are non-movably mounted in the laterally projecting proximal end portion 26 so as to overlie the cavity 24 as best seen in FIG. 2, and preferably are made in the form of an inverted U-shape. The transverse cutting edge 41 of the blade means 40 is substantially parallel to the plane of the upper edges 50, 52 of the sidewalls 30, 32, the minimum lateral distance between the cutting edge 41 and the upper edges 50, 52 of the sidewalls 30, 32 designated d, being the minimum depth of the tissue strip that may be taken from the endocervical canal of the patient.

The upper edges 50, 52 of sidewalls tend to act as guiding edges for the blade member 40. To facilitate the cutting of the strip of tissue 60, the blade means 40 is provided with a pair of generally vertical side cutting edges 43, 44 as viewed in transverse cross-section and which preferably slope rearwardly from the guiding edges 50, 52 to the transverse cutting edge 41. As shown by FIGS. 2, 4 and 5, all cutting edges 41, 43 and 44 are oriented towards distal end 22 of basket member 20. Thus, the side cutting edges 43, 44 form leading cutting edges, and the transverse cutting edge 41 is a trailing cutting edge when the instrument is used in a normal way that is, as it is drawn in a distal direction.

The side cutting edges 43, 44 also are preferably sloped so as to converge proximally as best seen in FIG. 4. The transverse cutting edge 41 is thus bounded by side cutting edges 43 and 44 at their point of minimum separation and has therefore a width that is of lesser distance than the maximum distance between the side cutting edges 43, 44 i.e., at the ends of the U structure. This particular blade configuration is preferable because of its greater ease of insertion into the endocervical canal.

Prior to the biopsy procedure, the patient is first locally anesthetized, as by a paracervical block. The instrument of this invention is then inserted within the endocervical canal with the laterally projecting blade means 40 extending just beyond the proximal tip of the canal and the edges 50, 52 of the sidewalls 30, 32 defining the entrance to the cavity 24 pressed against the lining of the endocervical canal. The blade means 40 is then moved distally along the endocervical lining towards the external os of the uterus with the edges 50, 52 of the sidewalls acting as guide members. The distal movement of the blade means 40 along the endocervical lining, as best shown in FIG. 3, cuts a strip 60 of endocervical tissue (of sufficient depth d, to include stroma) which strip 60 will fall, through the entrance into the cavity 24, in a coherent relatively clean mass.

Four endocervical biopsy strips are preferably obtained in successive cuts, following the above procedure. The resulting strips 60 are of a length equal to the endocervical canal, have a minimum width generally equal to the width of leading edge 41 of blade means 40, as measured between the side walls (e.g., preferably about 2.5 mm) and have a depth of about 1.5–2.0 mm. While the strip volume taken is considerably less than the cone-shaped portions taken in hospitalization procedures, and the amount of blood loss is substantially less, the strips taken do furnish the pathologist and physician with a sufficient amount of intact tissue on which to predicate an accurate diagnosis of both epithelial and stroma tissue extending the length of, and over a large portion of the circumference of the endocervical canal.

Each strip 60 of endocervical tissue may be readily removed from the basket member after the floor thereof is pivotally disengaged from its normally closed position.

After the above surgical procedure, the tissue of the endocervical canal is either chemically or electrocauterized in a conventional manner to prevent bleeding.

While the floor of the basket member is preferably pivotally mounted, as described, it may be rigidly mounted thereto, if desired. Other modifications of this invention will become apparent to those skilled in the art. Hence, I intend to be bound only by the claims which follow.

I claim:

1. An endocervical strip biopsy instrument which comprises:
    a handle means, an elongated basket member affixed to said handle means, said basket member having a wall surface defining an elongated cavity and an elongated entrance into said cavity generally coextensive therewith from an upper side of said basket member, said wall surface of said elongated cavity comprising a proximal end portion, a distal end portion including a back wall, sidewalls extending between said end portions, and a floor also extending between said end portions; and
    a non-movable, exposed continuous blade means, affixed to said proximal end, said continuous blade means having an exposed transversely extending cutting edge bounded by downwardly extending cutting edges adjacent to and overlying said entrance of said cavity, said blade means projecting above said sidewalls of said elongated cavity whereby said sidewalls act as guide members limiting insertion of said blade means into tissue to be cut, and all of said cutting edges of said blade means being oriented towards said distal end of said basket member, whereby tissue strips cut by said cutting edges will pass in a coherent mass into said cavity through said elongated entrance thereof as the instrument is drawn in a distal direction.

2. The endocervical strip biopsy instrument of claim 1 wherein said wall surface of said elongated cavity comprises a proximal end portion, a distal end portion, sidewalls extending between said end portions, and a floor also extending between said end portions, said floor being removably affixed to said end portions.

3. The endocervical strip biopsy instrument of claim 1 wherein said wall surface of said elongated cavity comprises a proximal end portion, a distal end portion, sidewalls extending between said end portions, and a floor also extending between said end portions, said floor being pivotally affixed to one of said end portions and removably affixed to the other of said end portions.

4. The endocervical strip biopsy instrument of claim 1 wherein the downwardly extending cutting edges form leading cutting edges and the transverse cutting edge is a trailing edge when said instrument is drawn in a distal direction.

5. The endocervical strip biopsy instrument of claim 1 wherein the transverse cutting edge has a width that is less than the maximum distance between the downwardly extending cutting edges.

* * * * *